United States Patent [19]

Phillips

[11] 4,329,999

[45] May 18, 1982

[54] PATIENT ATTACHED PATCH AND METHOD OF MAKING

[76] Inventor: Michael Phillips, Talcott Forest Rd., Apt. 3E, Farmington, Conn. 06032

[21] Appl. No.: 126,882

[22] Filed: Mar. 3, 1980

[51] Int. Cl.³ .......................................... B32B 31/18
[52] U.S. Cl. .................................. 128/760; 156/247;
 156/249; 156/250; 156/256; 156/263
[58] Field of Search ............... 156/250, 256, 263, 514,
 156/247, 249; 128/632, 637, 760, 762, 112, 113,
 290 P, 296

[56] References Cited

U.S. PATENT DOCUMENTS

3,289,671 12/1966 Troutman et al. ................. 128/760
4,190,060  2/1980 Greenleaf et al. ................ 128/760

*Primary Examiner*—Caleb Weston
*Attorney, Agent, or Firm*—Shoemaker and Mattare, Ltd.

[57] ABSTRACT

A patch which is attached to a patient to collect sweat is formed. The patch collects sweat from a patient in a non-intrusive manner which produces very accurate and precise results to determine the amount of drug and/or alcohol use by such patient.

52 Claims, 21 Drawing Figures

PATIENT ATTACHED PATCH AND METHOD OF MAKING

BACKGROUND OF THE INVENTION

The present invention relates in general to clinical test devices, and, more particularly, to patient monitoring devices.

A physician often must know the drug-related history of a patient. This history may include drug regimens prescribed by other physicians, and non-prescribed drug use. A very common history relates to use of alcohol by the patient.

These histories should be known with as much precision and accuracy as possible to permit the physician to work out a regimen or procedure of his own.

It is often the case, however, that the data presented the physician by the patient is inaccurate and imprecise.

There is, therefore, need for a device which permits a physician to accurately and precisely determine the amount of drugs and/or alcohol used by a patient. Such a device would enable a physician to accurately identify alcohol abusers, then to monitor the efficacy of any treatment designed to help such users reduce their alcoholic intake. This device should also be non-intrusive and permit rapid and early identification of the sought-after test results.

SUMMARY OF THE INVENTION

The device formed according to the method described herein is easy to use, non-intrusive and produces very accurate and precise measurements.

The patch is capable of collecting sweat in a continuous manner and at a steady rate. While the description presented herein is with regard to alcoholic beverage consumption, the patch can be used in any drug regimen, or the like, and this description is not intended to be limiting.

The tests using the device herein described can be carried out in a relatively rapid manner as compared to known tests, thereby permitting early identification of precise test results for the sought-after data.

Applications for this patch are therefore:

(1) In clinical practice, the test can be used to detect abusers of alcohol, and also monitor those who claim to be abstinent.

(2) In research, the test can be used in the evaluation of any therapy purported to help alcoholics drink less, and also as an epidemiologic tool to measure the drinking habits of groups (e.g., school children or the like).

(3) The patch can also detect numerous other drugs which are excreted in the sweat (e.g., digoxin, lithium, anticonvulsants, morphine, and the like). Hence, the patch can monitor compliance with a prescribed drug regimen (a difficult and common problem in medical practive) and also monitor the patient's intake of several drugs of abuse.

OBJECTS OF THE INVENTION

It is, therefore, an object of the present invention to produce a device which accurately and precisely measures drugs and/or alcohol consumption practices of a patient.

This together with other objects and advantages which will become subsequently apparent reside in the details of construction and operation as more fully hereinafter described and claimed, reference being had to the accompanying drawings forming part hereof, wherein like reference numerals refer to like parts throughout.

DETAILED DESCRIPTION OF THE INVENTION

Figures 1, 2, 3:
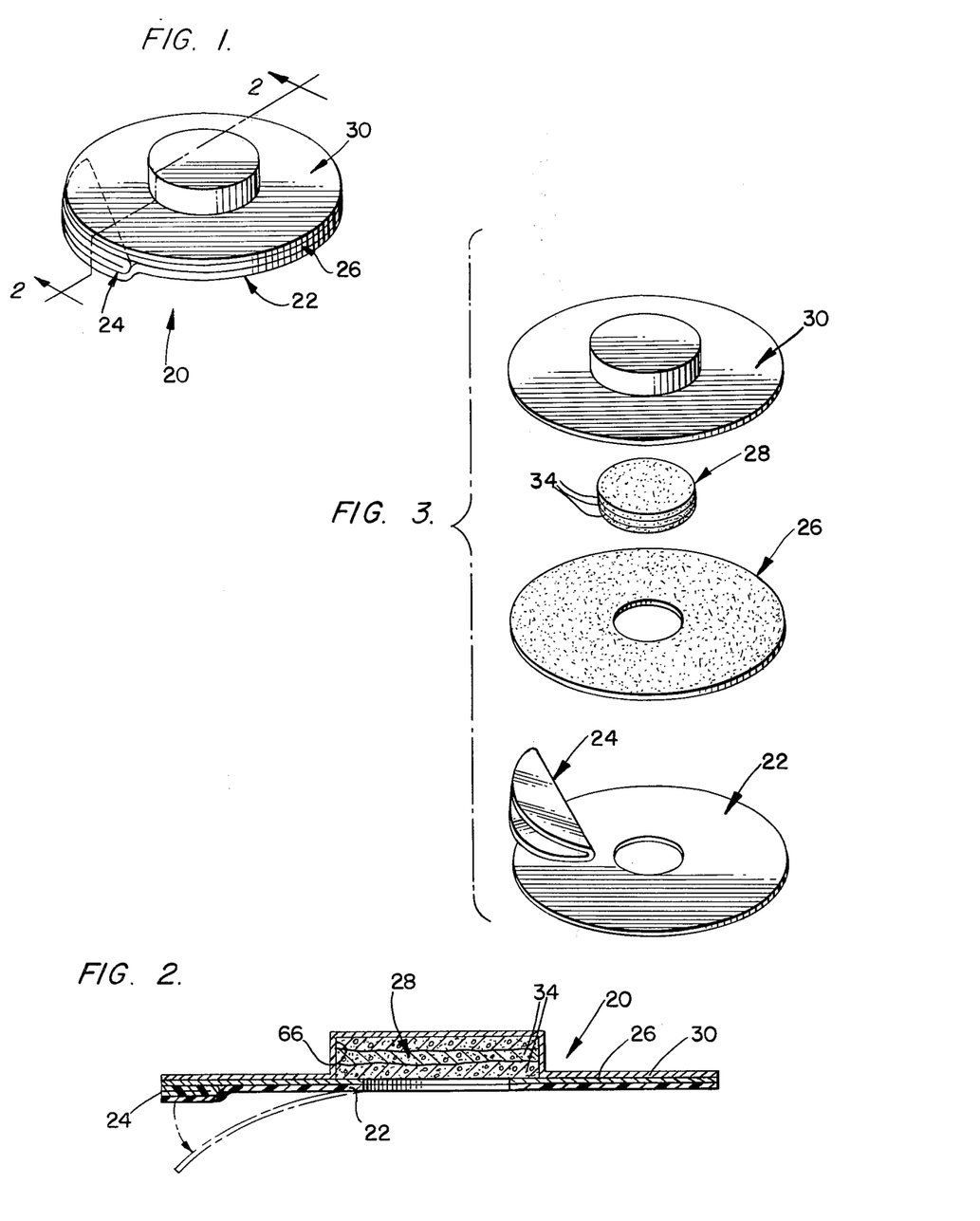
FIG. 1 is a perspective of a test patch formed according to the teachings of the present invention.
FIG. 2 is an elevation view taken along line 2—2 of FIG. 1.
FIG. 3 is an exploded perspective of a test patch formed according to the teachings of the present invention.
Figure 4:
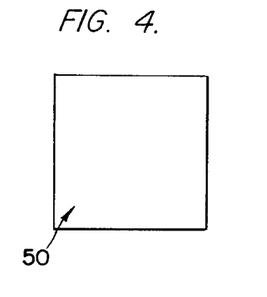
FIGS. 4–12 show steps used in carrying out a method embodying the teachings of the present invention.

Shown in FIGS. 1 and 3 is a patch 20 embodying the teachings of the present invention. The patch includes a backing member 22, a stripping member 24, a base 26, a collecting pad 28, and a cover member 30. FIGS. 1 and 3 show the patch in an assembled form. The patch is used as a diagnostic device, and, as above discussed, is extremely accurate and precise. The patch 20 is formed according to the steps shown in FIGS. 4–12, with the collecting pad 28 including a plurality of layers 34 of polyester-type material, or the like, and is formed according to a method shown in FIG. 13.

Referring to FIGS. 4–12, the method of forming patch 20 includes cutting a first portion of material into a square 50. The square 50 is preferably formed of polystyrene material, and is approximately 7 cm×7 cm in size. A first hole 52 is defined at or near the center of the first portion of material 50, and is formed by punching or the like. Preferably, the hole is 13/16 inches (20.6 mm) in diameter.

Figure 5:
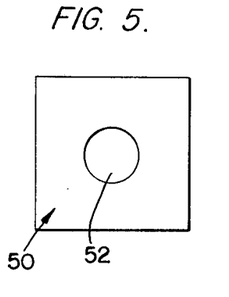

A strip of adhesive tape 54 is applied to the sheet to cover hole 52. The adhesive tape 54 is preferably a plastic-type tape, such as Hytape Surgical Tape, and is smooth surfaced. The tape is preferably 2 inches wide.

Figure 6:
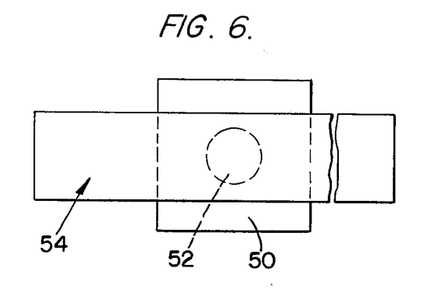
Figures 7, 8, 9, 10:
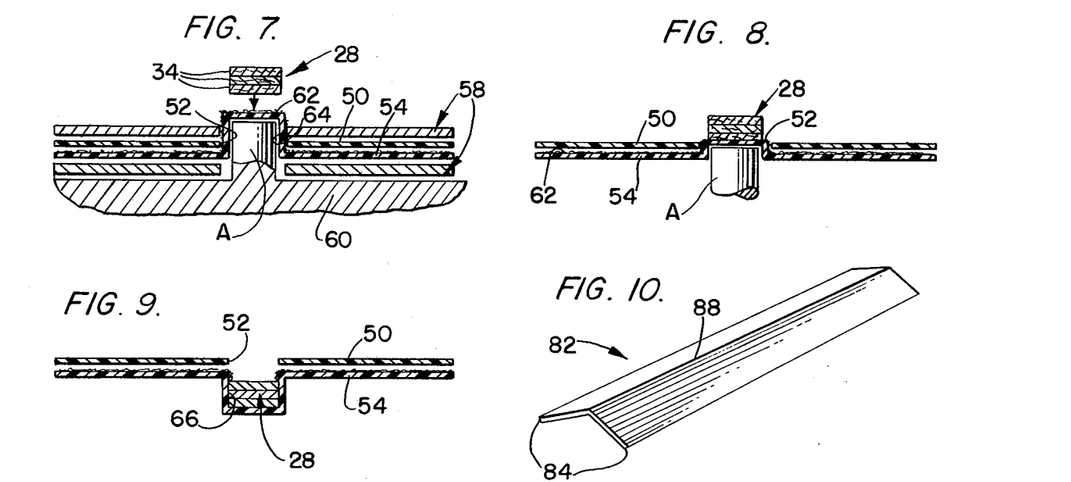

The strip covered intermediate element shown in FIG. 6 is sandwiched in a template 58, then heat shaped, preferably in a blast of hot air from a device such as a hair dryer or the like. It is noted that a punch 60 is used to force the adhesive strip 54 through hole 52 with the adhesive surface 62 facing outwardly of chamber 64 formed by the anvil A of the punch 60. It is noted that the subelement shown in FIG. 7 is maintained with the male punch in situ at least 48 hours to prevent the tape from resuming the shape shown therefor in FIG. 6.

Absorbent collecting pad 28 is applied to adhesive surface 62, and the chamber 64 is evaginated to define a chamber 66 with the pad 28 inside chamber 66. The male punch anvil A and a backing template can be used to firmly set the absorbent pad 28 in chamber 66. It is noted that adhesive surface 62 is upwardly presented in FIGS. 7, 8 and 9 and the evagination of the chamber is seen by comparing FIG. 8 with FIG. 9.

Figure 11:
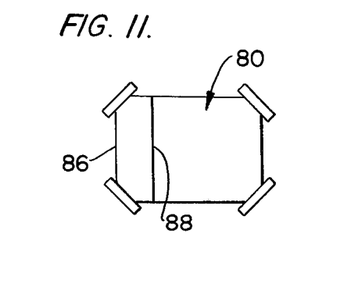

A second portion 80 (FIG. 11) of material is cut to define a square which is preferably 7 cm×7 cm and is preferably formed of a polystyrene material. A third portion 82 (FIG. 10) of material is also cut. The third portion of material is preferably a strip of vinyl film 2 cm wide. The portion 82 is folded longitudinally so that longitudinal ends 84 are coincident. The length of folded material 82 is attached to the portion of material 80, preferably by taping, and preferably so that longitudinal edges 84 of material 82 are coincident with one of the end edges 86 of the material 80. As shown in FIG. 11, foldline 88 of the material 82 is spaced from end edge 86 of the material 80. This step is preferably formed on a flat surface, and the folded material forms the stripping element 24 in the final patch to facilitate removal of the protective backing member 22.

Figure 12:
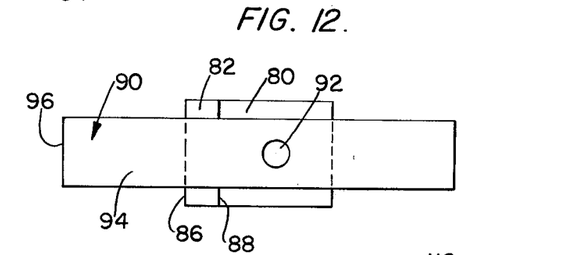

As shown in FIG. 12, a length of adhesive tape 90 is applied to the subelement shown in FIG. 11 to cover the folded portion 82 and the portion 80. The adhesive tape 90 is preferably a plastic-type tape such as Hytape Surgical Tape and is smooth surfaced and is preferably 2 inches wide. An access hole 92 is formed through the tape and the portion of material 80, preferably by stamping. The access hole 92 is preferably 9/16 inches (14.3 mm) in diameter, and is formed at or near the center of portion 80.

The shaped element shown in FIGS. 8 and 9 is stripped from the portion of material 50 and is applied to the subelement shown in FIG. 12 so that chamber 66 is coincident with access hole 92 and adhesive surface 62 adheres to top surface 94 of the adhesive tape 90 so that the adhesive tape 90 is interposed between the adhesive surface 62 and material portions 80 and 82. Access to chamber 66 is thus via access hole 92. Adhesive surface 96 of the tape 90 is presented into the plane of the paper in FIG. 12.

A disc, preferably 1⅝ inches (41.3 mm) in diameter is formed, preferably by stamping, out of the assembled element with the chamber containing pad at the center of the disc. The collecting patch is now complete.

It is noted that the relative sizes and orientation of hole 92 and chamber 66 (i.e., hole 52) permit sweat to easily enter the absorbent pad 28, but inhibit the reverse flow of sweat out of chamber 56.

Figure 13:
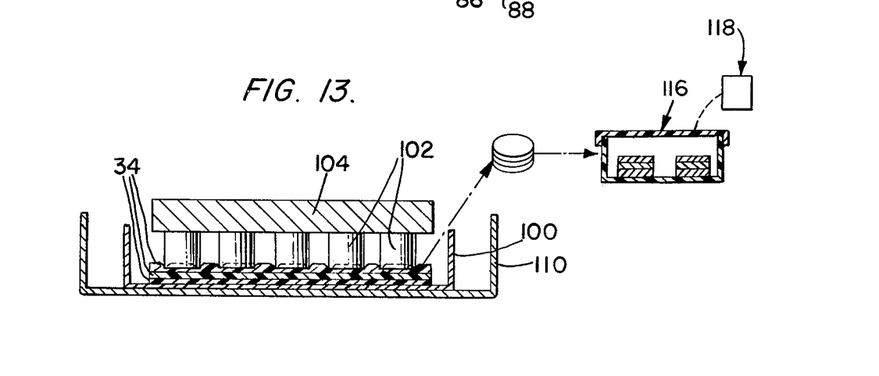
FIG. 13 shows a step of forming a portion of a test patch formed according to the teachings of the present invention.

The preferred method of forming the collecting pad 28 is shown in FIG. 13, and includes the steps of layering three similar sheets of felted polyester absorbent material 34 one on top of the other on a sheet of aluminum foil 100. The polyester is then thoroughly wetted with a saturated solution of sodium chloride in water. Preferably, the felted polyester absorbent material is 1½ denier polyester fiber, non-woven needle loomed with a 0.8% hydrophilic finish.

Aluminum caps 102, preferably 13/16 inches (20.6 mm) in diameter are placed on the wet polyester, and a weight 104, preferably a sheet of steel, is placed on top of the caps.

The aluminum foil and the material contained therein is situated in a tray 110, preferably before the weight is applied to the caps, and the tray is heated, preferably in an oven at 80° C. for 15 to 20 hours. It is noted that time and temperature are important in order to achieve optimal precipitation of the sodium chloride.

Discs are punched out from the dried polyester at the sites of grooves formed by the aluminum caps. Accordingly, in the preferred embodiment, the discs are 13/16 inches in diameter.

Discs 28' thus punched out are then wetted with a solution, preferably containing Nystatin, sodium fluoride and reduced methylene blue. This wetting step is performed in a glass dessicator 116 under $CO_2$, in order to avoid oxidizing the methylene blue. The discs are then dessicated to dryness at room temperature. Drying may be accelerated with a vacuum dryer 118. The patches thus formed are then incorporated into the adhesive patch described above. It is noted that the adhesive patch is waterproof.

The purpose of the additives is as follows:

Nystatin: Inhibits fungal proliferation. Fungi normally resident on the surface of the skin might otherwise contaminate the sweat specimen, causing (a) metabolic breakdown of ethanol (to acetaldehyde and water); and/or (b) metabolic breakdown of glucose in sweat, generating ethanol and methanol de novo.

Sodium fluoride: Inhibits anaerobic glycolysis in bacteria and fungi normally resident on skin. It provides a safeguard against any of these organisms contaminating the sweat with products of anaerobic glycolysis, e.g., ethanol.

Reduced methylene blue: In a wet patch this turns bright blue in the presence of oxygen. Hence it is a visual indicator (when the patch is removed) that the patch has leaked and/or been tampered with.

NOTE: The use of sodium chloride is not critical in this patch. It works equally well with a number of other agents, including magnesium sulfate, fructose and urea. The criterion, therefore, is that the element be an osmotically active highly soluble crystalloid.

As shown in FIG. 2, the backing member is removed and the patch 20 is applied to a patient to monitor a patient as above discussed.

TEST RESULTS

Figure 14:
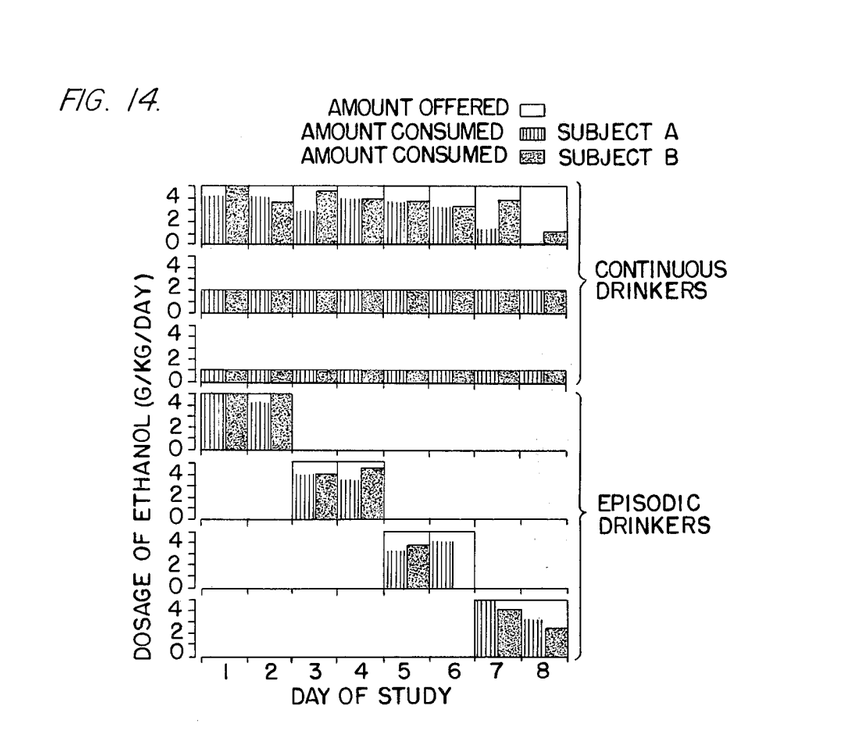
FIGS. 14–21 show results of tests using a test patch formed according to the teachings of the present invention.
Figure 15:
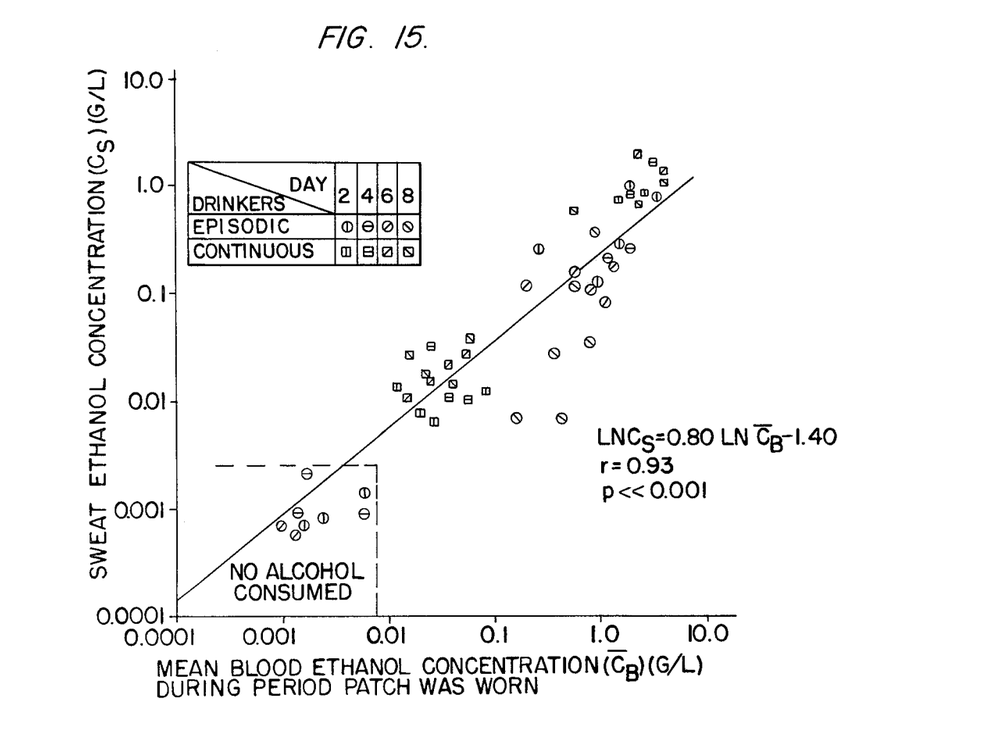
Figure 16:
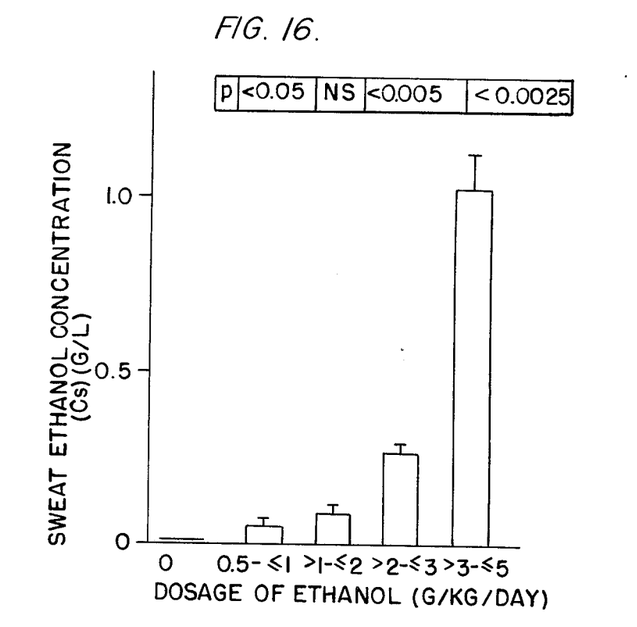
Figure 17:
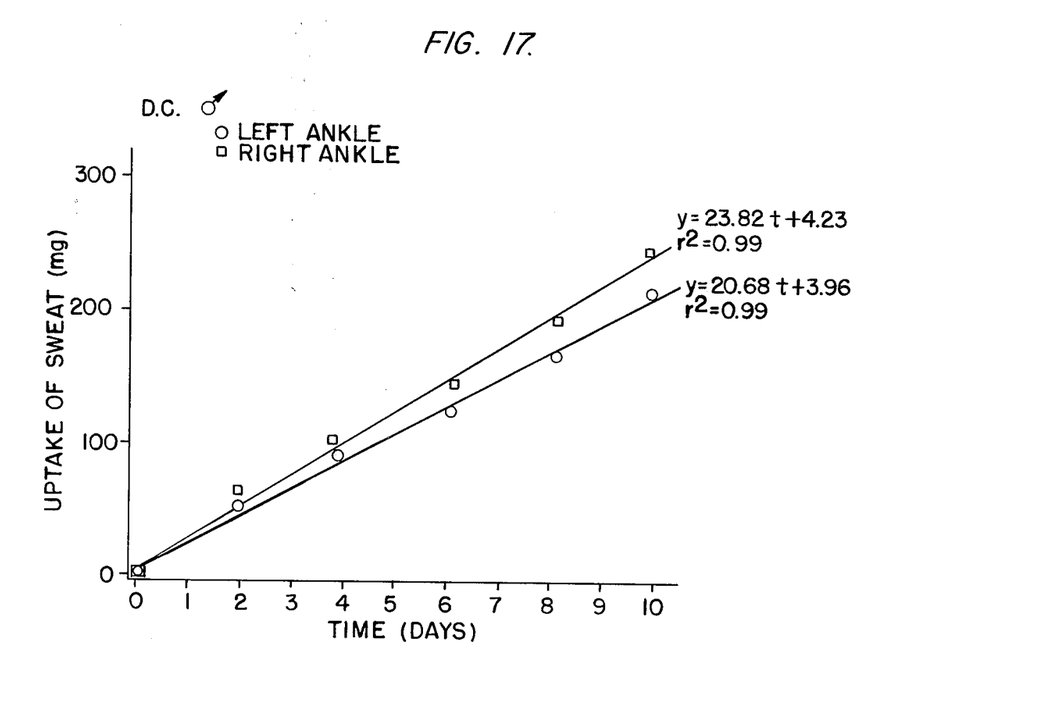
Figure 18:
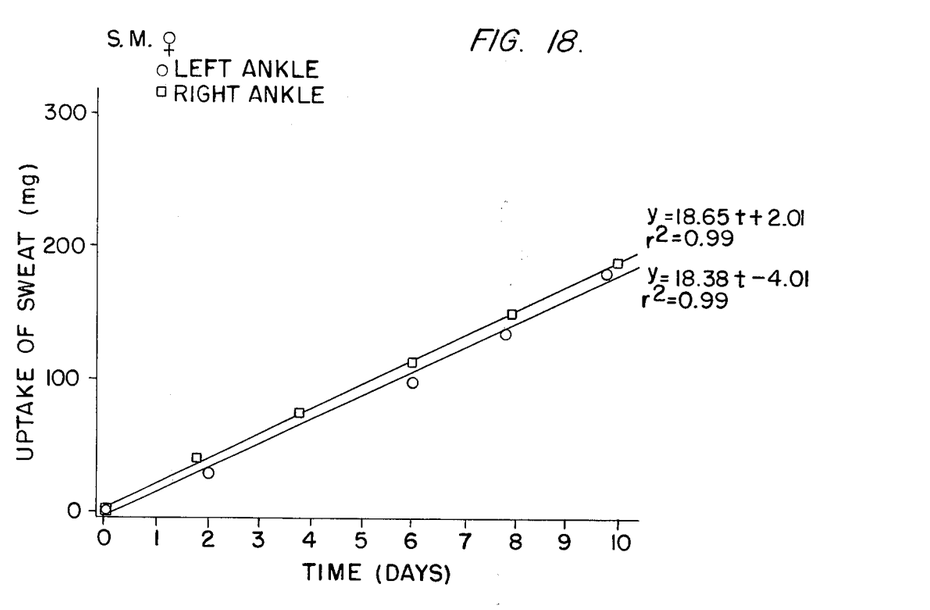
Figure 19:
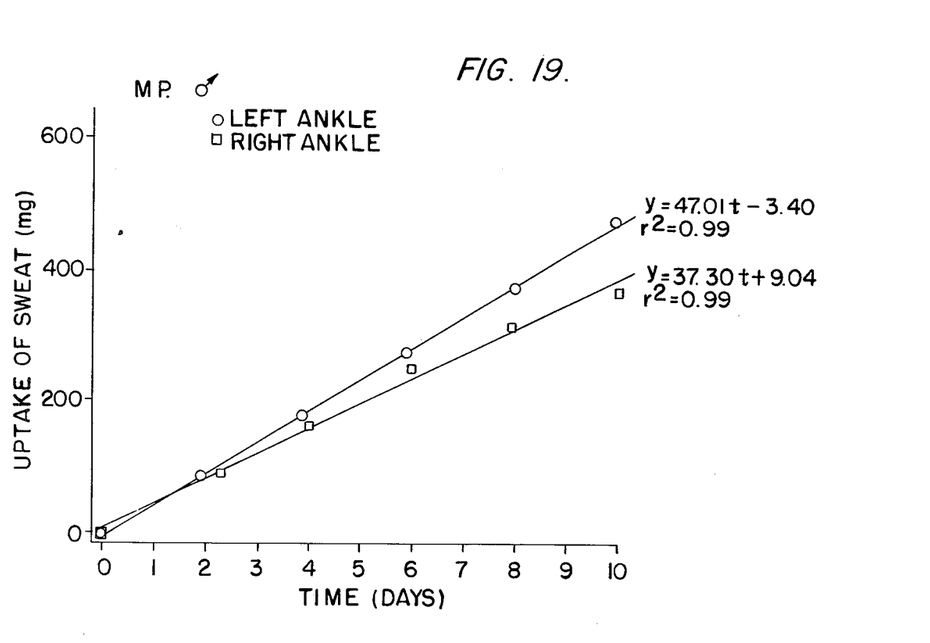
Figure 20:
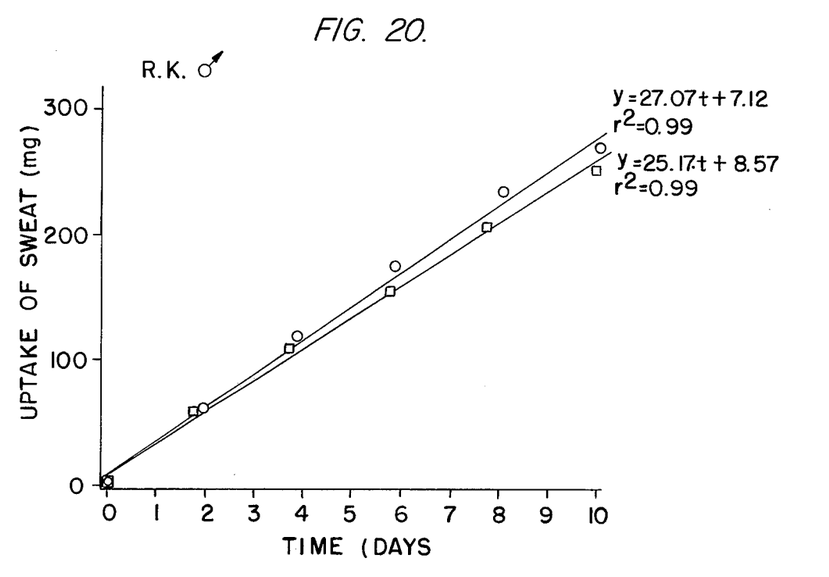

Patches formed as above discussed were used to evaluate alcohol consumption, and the results of these tests are presented in FIGS. 14–16. Volunteers consumed alcohol while wearing patches formed as above discussed. The volunteers wore the patches while drinking controlled amounts of alcoholic beverages over an eight-day period. It is noted that all of the volunteers were males aged between 34 and 71 (49.6±12.0) (mean±SD) who customarily drank alcoholic beverages every day. Under carefully controlled environments, all the volunteers received balanced diets plus multivitamin supplements.

The quantities of alcohol offered and consumed are shown in FIG. 14. Two subjects were allocated to each of seven different dosage groups: three groups of continuous drinkers and four groups of episodic drinkers. The continuous drinkers were offered 1.0, 2.0 or 5.0 G ethanol/kg/day for eight days, and the episodic drinkers were offered 5.0 G ethanol/kg/day for only two days and abstained the remaining six days.

All were offered the same beverage alcohol ("White Label" Scotch Whisky, John Dewar and Sons Ltd., Perth, Scotland) in quantities which did not exceed the amount of ethanol they claimed to have consumed each day over the preceding month. The whisky was served in divided doses at 10:00 a.m., 2:00 p.m., 6:00 p.m. and 10:00 p.m. Any left over from the preceding dose was taken away and the volume measured so that the actual amount consumed could be determined. All subjects were free to drink as much or as little as they wished of the offered whisky unless they became obviously intoxicated; then the dosage was reduced or withdrawn.

On the first morning of the study, each subject's legs were shaved with an electric clipper from knee to ankle, swabbed with isopropyl alcohol and allowed to dry. At 9:00 a.m., 16 sweat patches were affixed, eight to each leg.

The sweat patches were subsequently removed four at a time at 9:00 a.m., after two, four, six and eight days. The sweat was extracted, then stored at $-70°$ C. prior to assay for ethanol content.

Blood was collected from an indwelling venous catheter which was replaced every 48 hours. Every two hours for the eight day study, 2.0 ml of blood was taken from each subject into a sealed tube containing 17.5 mg sodium fluoride and 14 mg potassium oxalate (VACUTAINERS (R)). Aliquots were pooled in order to determine the mean blood ethanol concentration during the period each patch was worn, and stored at 4° C. until assayed.

A technician "blinded" to the experimental design assayed all specimens of sweat and pooled blood by a method of head-space gas chromatography. The concentration of ethanol in the sweat was calculated as the mean of the four patches simultaneously removed.

The results of the above-described test are shown in FIG. 15. As shown in that figure, in both continuous and episodic drinkers, there was a linear relationship between the concentration of ethanol in the sweat ($C_s$) and the mean concentration of ethanol in the blood ($\bar{C}_b$) during the period the sweat patches were worn (ln $C_s = 0.80$ ln $\bar{C}_b = 1.40$; $r = 0.93$, $p < < 0.001$).

Shown in FIG. 16 is the variation of the sweat-ethanol concentration with the dosages of ethanol. This figure incorporates the values observed in continuous and episodic drinkers on days 2, 4, 6 and 8 of the study. Each bar shows the mean sweat-ethanol concentration observed in a particular dosage range, plus S.E.M. The values observed in each dosage range were compared to those of the next lower dosage range (p determined by single-tailed t test).

The diagnostic value of any test for alcohol consumption is determined by its sensitivity, specificity, ability to distinguish different levels of drinking, and its acceptability in clinical practice.

Under the conditions of this study, it was found that the above-described sweat patch test was 100% sensitive and specific. With no overlap of results, it clearly distinguished between members of two separate groups: those who drank no alcohol at all, and those who drank at least 0.5 G ethanol/kg/day, either continuously or episodically.

Assuming that these findings are applicable to alcohol consumption outside the laboratory, a test using the patch 20 similar to the above-described sweat patch test should detect a 70 kg drinker consuming an average of three fluid ounces of 100-proof spirits a day, or the equivalent amount of alcohol.

The sweat patch test also distinguished different levels of alcohol drinking. Regardless of whether the subject had been drinking continuously or episodically, the sweat ethanol concentration increased progressively with the average amount consumed daily and also rose linearly with the mean concentration of ethanol in the blood during the period the sweat patch was worn.

The sweat patch test appears to be acceptable in clinical practice. The only obvious limitations to its use are allergy to adhesive tape and a patient's willingness to cooperate. During the above-described test, no adverse local skin reactions nor any discomfort beyond transient itching were observed. The sweat patch is inexpensive and can be made relatively tamper-proof by such stratagems as incorporating a collorless reduced dye, e.g., methylene blue, which oxidizes to bright blue in the event of leakage or surreptitious removal. When applied carefully to the skin, accidental leakage of the sweat patch are rare, even during bathing or vigorous exercise.

Results of another test using the above-described test patch are shown in FIGS. 17-21, inclusively. In this test, four volunteers wore two patches for ten days. All were laboratory workers aged between 25 and 35, in good health and leading normal, active lives. The patches were applied to an area of skin previously shaved with an electric clipper, swabbed with isopropyl alcohol and allowed to dry. The area selected was the outer ankle, 10 cm above the lower border of the lateral malleolus. A piece of 2 inch MICROPORE (R) tape was applied to cover the whole patch and the adjoining skin. Every second day, the MICROPORE (R) tape and cover 32 were removed and the collecting pad 28 was placed in a sealed container and weighed on an analytical microbalance and the time noted. The pad was then immediately returned to cover the hole in the base 26 and sealed in place with a fresh cover 32 and length of MICROPORE (R) tape. The entire elapsed time required for removal, weighing and resealing of the pad was less than 3 minutes, a period which appeared not to permit significant loss of sweat from the pad by evaporation.

Figure 21:
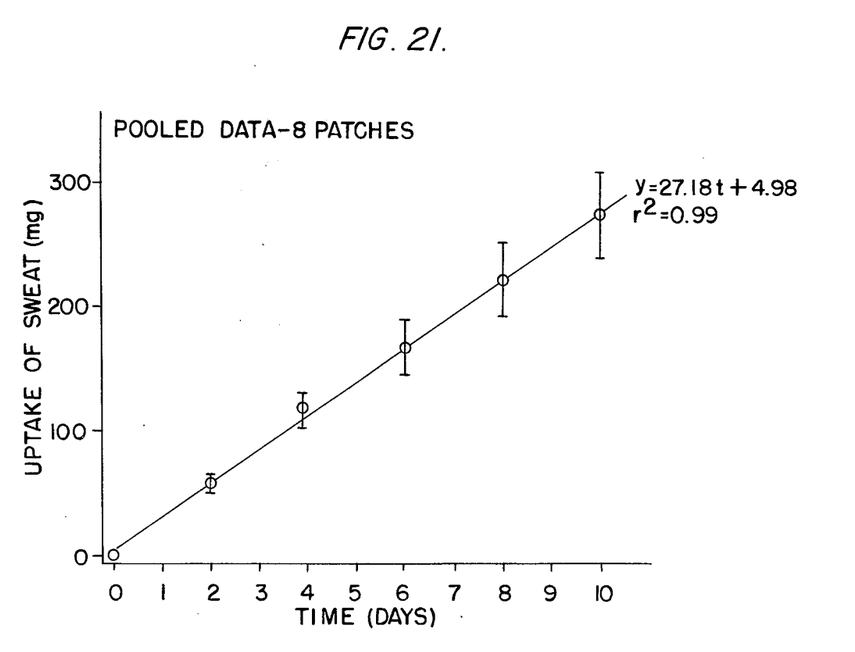

The uptake of sweat was calculated by subtracting the dry weight of each pad from its subsequent weights. Sweat uptake was plotted against time and the line of best fit was calculated by a linear regression program, and the uptake of sweat with time is shown for the four subjects in FIGS. 17-20. Pooled data from 8 patches are shown in FIG. 21.

The results of the just-described test demonstrate that the patch is capable of collecting sweat continuously at a steady rate for a period up to 10 days. The uptake rate varies from site to site, and person to person. However, it appears to be steady at a particular site upon a particular person.

This patch is convenient to apply, well tolerated by wearers, and yields virtually all of the collected sweat when spun in a specially constructed centrifuge tube such as described in Phillips, M., Vandervoort, R. E. and Becker, C. E., "Long-term Sweat Collection Using Salt-impregnated Pads", *J. Invest. Dermatol,* 68:221-224, 1977.

The patch above-described provides an inexpensive, non-invasive tool for the continuous collection of a body fluid which may then be assayed for its contents of drugs (e.g., ethanol, or the like) or other substances. It has potential applications in both research and clinical practice as a tool to monitor drug-taking programs and behavior.

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

I claim:

1. A method of forming a test patch for use in clinical studies including the steps of:
   cutting a first portion of material;
   defining a hole in said portion of material;

placing a strip of adhesive tape on said first portion of material to cover said hole;

heat shaping said strip covered first portion and forcing the adhesive surface of the adhesive tape through said hole;

placing an absorbent pad on the adhesive surface forced through said hole;

forcing said pad covered adhesive surface back through said hole so that said pad is located within a chamber defined by said adhesive strip;

cutting a second portion of material;

cutting a third portion of material;

folding said third portion of material;

attaching said folded portion of material to said second portion of material;

applying a length of adhesive tape to said second and third portions of material;

defining an access hole through said length of adhesive tape and said second portion of material;

removing said chamber containing adhesive tape from said first portion of material; and applying said chamber containing adhesive tape to said second portion of material so that said access hole is aligned with said chamber to form a combined portion of material.

2. The method defined in claim 1 wherein said first portion of material is cut into a square shape.

3. The method defined in claim 1 wherein said first portion of material is formed of polystyrene.

4. The method defined in claim 2 wherein said hole is defined at the center of said first portion of material.

5. The method defined in claim 1 wherein the hole in said first portion of material is circular and is approximately 13/16 inches in diameter.

6. The method defined in claim 1 wherein said strip of adhesive tape is formed of surgical tape.

7. The method defined in claim 1 wherein said heat shaping step includes placing said strip covered first portion of material in a template.

8. The method defined in claim 7 wherein said heat shaping step includes directing a blast of hot air onto said template located strip covered first portion of material.

9. The method defined in claim 8 wherein said heat shaping step includes maintaining said template located strip covered first portion of material in situ for at least forty-eight hours.

10. The method defined in claim 1 wherein said second portion of material is cut into a square shape.

11. The method defined in claim 1 wherein said second portion of material is formed of a polystyrene material.

12. The method defined in claim 10 wherein said third portion of material is formed of a strip of vinyl film.

13. The method defined in claim 12 wherein said third portion of material is folded longitudinally.

14. The method defined in claim 1 wherein said folded third portion of material is attached to said second portion of material near the edge of said second portion of material.

15. The method defined in claim 1 wherein said length of adhesive tape is formed of surgical tape.

16. The method defined in claim 1 wherein said access hole is defined near the center of said length of adhesive tape.

17. The method defined in claim 1 wherein said access hole is about 9/16 inches in diameter.

18. The method defined in claim 1 wherein said access hole is defined by stamping.

19. The method defined in claim 1 further including stamping a disc from said combined portion of material.

20. The method defined in claim 19 wherein said disc is about $1\frac{5}{8}$ inches in diameter.

21. The method defined in claim 1 further including forming said absorbent pad using steps including: layering a plurality of sheets of absorbent material one on top of the other; wetting said layered sheets; placing cylinders on said wet material; placing a weighting element on top of said cylinders; heating said weighted layered sheets; removing portions of said heated layered sheets; and wetting said portions.

22. The method defined in claim 21 wherein said sheets are formed of felted polyester absorbent material.

23. The method defined in claim 22 wherein said material is $1\frac{1}{2}$ denier, polyester fiber, non-woven needle loomed with a 0.8% hydrophilic finish.

24. The method defined in claim 21 further including a step of providing a container and said sheets are layered in said container.

25. The method defined in claim 24 wherein said container is formed of aluminum foil.

26. The method defined in claim 21 wherein said sheets are wetted with a saturated solution of sodium chloride in water.

27. The method defined in claim 21 wherein said cylinders have aluminum caps thereon.

28. The method defined in claim 21 wherein said cylinders are about 13/16 inches in diameter.

29. The method defined in claim 21 wherein said weighting element is formed of a sheet of steel.

30. The method defined in claim 21 wherein said heating step is performed at about 80° C. for about 15-20 hours.

31. The method defined in claim 21 wherein said removed portions are punched out.

32. The method defined in claim 21 wherein said removed portions are discs about 13/16 inches in diameter.

33. The method defined in claim 21 wherein said removed portions are wetted with a solution containing Nystatin, sodium fluoride and reduced methylene blue.

34. The method defined in claim 33 wherein wetting of said removed portions is performed in a glass dessicator under $CO_2$.

35. The method defined in claim 34 further including a step of dessicating said wetted removed portions to dryness at room temperature.

36. The method defined in claim 35 further including a step of accelerating drying of said wetted removed portions using a vacuum dryer.

37. A test patch formed according to the method defined in claim 1.

38. A test patch as defined in claim 37 wherein said first portion of material is formed of polystyrene.

39. A test patch as defined in claim 37 wherein said hole is defined at the center of said first portion of material.

40. A test patch as defined in claim 37 wherein the hole in said first portion of material is circular and is approximately 13/16 inches in diameter.

41. A test patch as defined in claim 37 wherein said strip of adhesive tape is formed of surgical tape.

42. A test patch as defined in claim 37 wherein said second portion of material is cut into a square shape.

43. A test patch as defined in claim 37 wherein said second portion of material is formed of a polystyrene material.

44. A test patch as defined in claim 37 wherein said third portion of material is formed of a strip of vinyl film.

45. A test patch as defined in claim 37 wherein said length of adhesive tape is formed of surgical tape.

46. A test patch as defined in claim 37 wherein said access hole is defined near the center of said length of adhesive tape.

47. A test patch as defined in claim 37 wherein said access hole is about 9/16 inches in diameter.

48. A test patch as defined in claim 37 wherein said absorbent pad includes a plurality of sheets of absorbent material layered one on the other, and wetting solution wetting said layers.

49. A test patch as defined in claim 48 wherein said sheets are formed of felted polyester absorbent material.

50. A test patch as defined in claim 48 wherein said material is 1½ denier, polyester fiber, non-woven needle loomed with a 0.8% hydrophilic finish.

51. A test patch as defined in claim 48 wherein said wetting solution includes a solution of sodium chloride in water.

52. A test patch as defined in claim 48 wherein said wetting solution includes a solution containing Nystatin, sodium fluoride and reduced methylene blue.

* * * * *